United States Patent [19]

Weyer et al.

[11] 4,379,785
[45] Apr. 12, 1983

[54] HETEROCYCLIC SUBSTITUTED SULFONYL UREAS, AND THEIR USE

[75] Inventors: Rudi Weyer, Kelkheim; Volker Hitzel, Hofheim am Taunus; Karl Geisen, Frankfurt am Main; Günter Regitz, Bad Soden am Taunus, all of Fed. Rep. of Germany

[73] Assignee: Hoechst Aktiengesellschaft, Frankfurt am Main, Fed. Rep. of Germany

[21] Appl. No.: 217,524

[22] Filed: Dec. 17, 1980

[30] Foreign Application Priority Data

Dec. 19, 1979 [DE] Fed. Rep. of Germany ....... 2951135

[51] Int. Cl.³ .................... A61K 31/40; A61K 31/44; C07D 207/38; C07D 209/46
[52] U.S. Cl. ......................... 424/244; 260/239.3 R; 260/239.3 B; 424/258; 424/263; 424/267; 434/274; 546/141; 546/156; 546/203; 546/205; 546/206; 546/221; 546/243; 546/292; 548/512; 548/528; 548/538
[58] Field of Search .............. 260/326.23, 325 PH, 260/325 R, 239.3 R, 239.3 B; 564/40, 41; 546/203, 205, 141, 11 E, 221, 206, 292, 243, 156; 424/244, 274, 263, 267, 258

[56] References Cited

U.S. PATENT DOCUMENTS

| | | | |
|---|---|---|---|
| 3,336,322 | 8/1967 | Weber et al. | 546/226 |
| 3,510,496 | 5/1970 | Aumuller et al. | 260/325 PH |
| 3,646,009 | 2/1972 | Winter et al. | 564/41 |
| 3,655,756 | 4/1972 | Weber et al. | 564/41 |
| 3,819,633 | 6/1974 | Ambrogi et al. | 546/146 |
| 3,962,244 | 6/1976 | Weyer et al. | 260/256.5 R |
| 4,282,239 | 8/1981 | Weyer et al. | 424/274 |

FOREIGN PATENT DOCUMENTS

| | | |
|---|---|---|
| 1670700 | 3/1970 | Fed. Rep. of Germany . |
| 2103118 | 8/1972 | Fed. Rep. of Germany . |
| 2085759 | 3/1971 | France . |

OTHER PUBLICATIONS 79102066.2, European Patent Application Published Jan. 1, 1980 (=AD).

*Primary Examiner*—Alton D. Rollins
*Attorney, Agent, or Firm*—Curtis, Morris & Safford

[57] ABSTRACT

What are disclosed are sulfonyl ureas of the formula

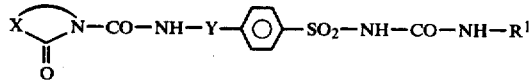

in which $R^1$, X and Y are as defined in the specification, and their physiologically acceptable salts, pharmaceutical formulations on the basis of these compounds, and their use in the treatment of diabetes.

6 Claims, No Drawings

HETEROCYCLIC SUBSTITUTED SULFONYL UREAS, AND THEIR USE

The invention relates to sulfonyl ureas of the formula

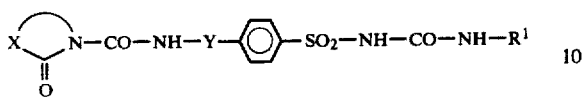

which, as such or in the form of their physiologically acceptable salts, have hypoglycemic properties and are distinguished by a pronounced lowering of the blood sugar level, and can therefore be used as medicaments.

In the formula

X is alkylene or alkenylene having from 3 to 6 carbon atoms, optionally substituted by up to 3 alkyl groups each having from 1 to 4 carbon atoms, or a phenyl radical; or cycloalkylenealkyl having up to 3 carbon atoms in the alkyl moiety and from 5 to 7 ring carbon atoms, optionally substituted by up to 3 methyl groups, or unsaturated;

Y is alkylene having 2 or 3 carbon atoms;

$R^1$ is alkyl having from 4 to 6 carbon atoms, cycloalkyl, alkylcycloalkyl, dialkylcycloalkyl, cycloalkylalkyl, cycloalkenyl or alkylcycloalkenyl with in each case 4 to 9 C atoms, methylcyclopentylmethyl, cyclohexenylmethyl, chlorocyclohexyl, methoxycyclohexyl, bicycloheptyl, bicycloheptenyl, bicycloheptylmethyl, bicycloheptenylmethyl, bicyclooctyl, nortricyclyl, adamantyl or benzyl.

In the formula, X is preferably an alkylene or alkenylene radical having 3 or 4 carbon atoms and substituted by 1 to 2 $C_1$-$C_2$-alkyl groups, Y is —$CH_2$—$CH_2$— or —CH—$CH_2$, the $CH_2$—$CH_2$— group being particularly preferred. $CH_3$ $R^1$ is preferably methylcyclopentyl, cyclopentylmethyl, cyclohexyl, 4-methyl-, 4-ethyl- or 4-isopropyl-cyclohexyl.

Possible bicyclic radicals are: bicyclo[2.2.1.]heptyl, bicyclo[2.2.1.]-heptylmethyl and the corresponding unsaturated radicals, and the bicyclo[2.2.2.]octyl radical.

The invention furthermore relates to processes for the manufacture of these sulfonyl ureas, pharmaceutical preparations which contain them or consist of them and their use for the treatment of diabetes.

The processes for the manufacture comprise (a) reacting benzenesulfonyl-isocyanates, -carbamic acid esters, -thiolcarbamic acid esters, -ureas, -semicarbazides or -semicarbazones each substituted by the group

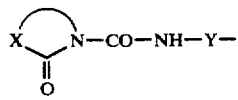

in the 4-position, with an amine $R^1$-$NH_2$ or salts thereof, or reacting sulfonamides of the formula

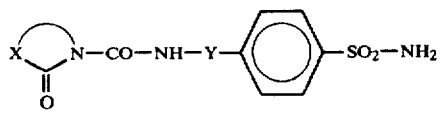

or salts thereof with $R^1$-substituted isocyanates, carbamic acid esters, thiolcarbamic acid esters, carbamic acid halides or ureas, (b) splitting benzenesulfonylisourea ethers, -isothiourea ethers, -parabanic acids or -halogenoformic acid amidines, each substituted by the

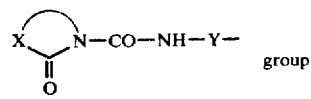 group or benzenesulfonyl ureas substituted by the

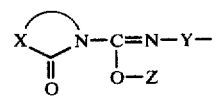

group, where Z is alkyl having 1 or 2 carbon atoms;

(c) replacing the sulfur atom in benzenesulfonylthioureas substituted by

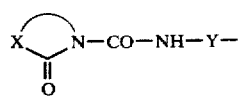

by oxygen, (d) oxidizing corresponding benzene-sulfinyl- or -sulfenylureas, (e) introducing the radical

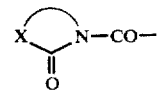

if appropriate stepwise, into benzenesulfonylureas of the formula

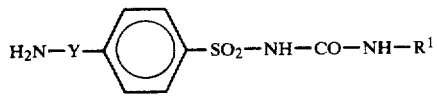

(f) reacting correspondingly substituted benzenesulfonyl halides with $R^1$-substituted ureas or alkali metal salts thereof, or reacting correspondingly substituted benzenesulfinic acid halides or, in the presence of acidic condensing agents, also correspondingly substituted sulfinic acids or alkali metal salts thereof with N-$R^1$-N'-hydroxyurea, and, if appropriate, treating the reaction products with alkaline agents in order to form salts.

The benzenesulfonyl-carbamic acid esters and -thiolcarbamic acid esters mentioned can contain an alkyl radical, an aryl radical or a heterocyclic radical in the alcohol component. Since this radical is split off during the reaction, its chemical structure does not influence the character of the end product and can therefore be varied within wide limits. The same is true of the N-$R^1$-substituted carbamic acid esters and the corresponding thiolcarbamic acid esters.

Suitable carbamic acid halides are, above all, the chlorides.

The benzenesulfonylureas which are possible starting substances for the process can be unsubstituted, monosubstituted or, in particular, disubstituted on the side of the urea molecule opposite the sulfonyl group. Since these substituents are split off during the reaction with amines, their character can be varied within wide limits. Besides benzenesulfonylureas substituted by alkyl, aryl, acyl or heterocyclic substituents, it is also possible to use benzenesulfonylcarbamoylimidazoles and similar compounds or bisbenzenesulfonylureas, which can also carry a further substituent, for example methyl, on one of the nitrogen atoms. For example, it is possible to treat such bis-(benzenesulfonyl)-ureas or N-benzenesulfonyl-N'-acylureas with $R^1$-substituted amines and to heat the resulting salts to elevated temperatures, in particular to temperatures above 100° C.

It is furthermore possible to use $R^1$-substituted ureas or those $R^1$-substituted ureas which are also monosubstituted or, in particular, disubstituted on the free nitrogen atom as the starting materials, and to react these with benzenesulfonamides which are substituted in 4-position by

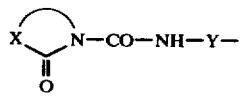

Possible starting substances of this type are, for example, N-cyclohexyl-urea, the corresponding N'-acetyl-, N'-nitro-, N'-cyclohexyl-, N',N'-diphenyl- (in which the two phenyl radicals can also be substituted and linked with one another directly or via a bridge member, such as —CH$_2$—, —NH—, —O— or —S—), N'-methyl-N'-phenyl- and N',N'-dicyclohexyl-ureas, and cyclohexyl-carbamoylimidazoles, -pyrazoles or -triazoles, as well as those of the compounds mentioned which, instead of cyclohexyl, carry another substituent within the range of the definition of $R^1$.

The benzenesulfonyl-parabanic acids, -isourea ethers, -isothiourea ethers or -halogenoformic acid amidines mentioned as starting substances are appropriately split by alkaline hydrolysis. Isourea ethers can also be split successfully in an acidic medium.

The replacement of the sulfur atom in the thiourea grouping of correspondingly substituted benzenesulfonylthioureas by an oxygen atom can be carried out in known manner, for example with the aid of oxides or salts of heavy metals, or by using oxidants, such as hydrogen peroxide, sodium peroxide, nitrous acid or permanganates. The thioureas can also be desulfurized by treatment with phosgene or phosphorous pentachloride. Chloroformic acid amidines or carbodiimides obtained as intermediate stages can be converted into the benzenesulfonylureas by suitable measures, such as saponification or adding on of water.

The oxidation of benzenesulfinylureas and benzenesulfenylureas is carried out by known methods, preferably with oxidants, such as permanganate or hydrogen peroxide.

The acylation of the sulfonylureas according to process (e) can be carried out with reactive derivatives of the acid

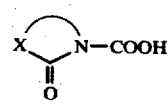

such as, for example, halides.

Suitable sulfonyl halides and sulfinyl halides according to process (f) are, in particular, the chlorides. Thionyl chloride or polyphosphoric acid, for example, can be employed as the acidic condensing agent.

The physiologically acceptable salts are manufactured by known methods. Alkali metal hydroxides, carbonates or bicarbonates and alkaline earth metal hydroxides, carbonates or bicarbonates and physiologically acceptable organic bases are particularly suitable for salt formation.

The embodiments of the process according to the invention can in general be varied greatly with regard to the reaction conditions and adapted to the particular circumstances. For example, the reactions can be carried out in the absence or presence of solvents, and at room temperature or at elevated temperature.

Depending on the character of the starting substances, one or other of the processes described may in particular give only low yields of an intended benzenesulfonyl urea, or be unsuitable for the synthesis of this compound. In such cases, which occur relatively rarely, the expert has no difficulty in synthetizing the desired product by another of the process routes described.

The resulting compound can be purified by reprecipitation and/or recrystallization. They can also be purified by liberating the substance from a crystalline (alkali metal) salt in a suitable solvent.

The compounds according to the invention are distinguished by valuable pharmacological properties, in particular by hypoglycemic properties. They are therefore suitable for use as medicaments, in particular as antidiabetic agents.

The hypoglycemic action of the benzenesulfonyl ureas described can be demonstrated by feeding them, as free compounds or in the form of the sodium salts, to rabbits on a normal diet, and determining the blood sugar value over a prolonged period of time in accordance with the known method of Hagedorn-Jensen or using an autoanalyzer.

The hypoglycemic action can be determined in a routine manner using doses of, for example, 10, 2 or 0.4 mg of active substance per kg of test animal according to known methods.

The following compounds I to III were administered orally in doses of 2 mg/kg to rabbits and the blood sugar values were determined over a prolonged period of time using an autoanalyzer. The lowering in the blood sugar level measured here is given in % after a given number of hours as specified in the following table.

I. N-(4-[2-(3-ethyl-4-methyl-2-oxo-3-pyrroline-1-carboxamido)-ethyl]-benzenesulfonyl)-N'-cyclohexyl urea II. N-(4-[2-(3-ethyl-4-methyl-2-oxo-3-pyrroline-1-carboxamido)-ethyl]-benzenesulfonyl)-N'-4-methylcyclohexyl urea III. N-(4-[2-(3,4-dimethyl-2-oxo-3-pyrroline-1-carboxamido)-ethyl]-benzenesulfonyl)-N'-4-methylcyclohexylurea

TABLE

| Compound | Lowering in the blood sugar level in rabbits after oral administration of 2 mg/kg, in % after | | | | | | | |
|---|---|---|---|---|---|---|---|---|
| | 1 | 3 | 6 | 24 | 48 | 72 | 92 | 120 hours |
| I | 34 | 45 | 37 | 44 | 32 | 0 | | |
| II | 24 | 35 | 36 | 33 | 34 | 8 | 0 | |
| III | 32 | 34 | 38 | 41 | 68 | 41 | 25 | 17 |

The acylureido-alkylbenzenesulfonyl ureas according to the invention are distinguished by a powerful hypoglycemic action. Furthermore, the compounds are well tolerated.

The properties of the compounds permit therapy of diabetes mellitus to be achieved with such low doses that the formulation only re-normalizes the reduced responsiveness of the pancreas to an increased blood sugar level.

Benzenesulfonyl ureas containing a ureidoalkyl radical have already been described several times (German Auslegeschrift No. 1,670,700, German Patent Specification Nos. 1,443,911, 1,618,389 and 2,238,870). It was not to be expected that the compounds according to the invention are distinguished by the abovementioned favorable properties.

The sulfonyl ureas according to the invention are intended, preferably, to be used for the manufacture of formulations which can be administered orally for the treatment of diabetes mellitus. They can be administered as such or in the form of their salts, or in the presence of substances which lead to salt formation. Alkaline agents, such as alkali metal hydroxides, carbonates or bicarbonates or alkaline earth metal hydroxides, carbonates or bicarbonates, for example, can be used for salt formation. In addition to the sulfonyl urea or a salt thereof, the formulation can furthermore also contain other active compounds.

Suitable medicament formulations are preferably tablets containing the usual carriers and auxiliaries such as talc, starch, lactose or magnesium stearate in addition to the sulfonyl ureas or the salts thereof. It may be advantageous to use the active substance(s) in ground or finely dispersed form, or as a mixture of these two forms.

A preparation which contains as active substance the benzenesulfonyl ureas described, for example a tablet or a powder with or without additives, is appropriately brought into a suitably dosed form. The dose to be chosen is that which is matched with the activity of the benzenesulfonyl urea used and with the desired effect. The dosage is appropriately about 0.5 to 50 mg, preferably 1 to 20 mg, per unit, but dosage units which are above or below this amount and which, if necessary, can be divided or multiplied before administration can also be used.

The following examples show some of the numerous process variants which can be used for the synthesis of the sulfonyl ureas according to the invention. However, they are not intended to represent a limitation of the subject of the invention.

EXAMPLE 1

N-(4-[2-(2-oxo-pyrrolidine-1-carboxamido)-ethyl]-benzenesulfonyl)-N'-cyclohexyl urea 47 g of 2-oxo-pyrrolidine-1-[N-2-phenyl-ethyl]-carboxamide (m.p. 88°-90° C., prepared from pyrrolidone and 2-phenylethyl isocyanate) are introduced with cooling and agitation into 95 g of chlorosulfonic acid. Subsequently, the batch is heated for 1 hour at 50° C., poured onto ice after cooling, the sulfochloride is separated and treated with concentrated ammonia. The sulfonamide is suction-filtered and recrystallized from butyl acetate/methylglycol; m.p. 178°-180° C.

5 g of 4-[2-(oxo-pyrrolidine-1-carboxamido)-ethyl]-benzenesulfonamide are dissolved in 100 ml of acetone with 0.65 g of NaOH and water. 2.3 g of cyclohexyl-isocyanate are added dropwise with agitation and ice cooling, and agitation is continued for 2 hours at room temperature. Subsequently, the substantial amount of acetone is distilled off under reduced pressure, the aqueous solution is acidified and the product is re-precipitated from dilute ammonia. The N-(4-[2-(2-oxo-pyrrolidine-1-carboxamido)-ethyl]-benzenesulfonyl)-N'-cyclohexyl urea is recrystallized from dilute ethanol, and has a melting point of 189°-190° C.

In analogous manner, there is obtained:
N-(4-[2-(2-oxo-pyrrolidine-1-carboxamido)-ethyl]-benzenesulfonyl)-N'-4-methyl-cyclohexyl urea
m.p. 179°-181° C. (from dil. ethanol).

EXAMPLE 2

N-(4-[2-(2-oxo-piperidine-1-carboxamido)-ethyl]-benzenesulfonyl)-N'-cyclohexyl urea 50.4 g of piperidine-(2) and 73 g of β-phenylethyl isocyanate are heated for 2 hours at 150° C. in an oil bath. The clear melt is cooled, treated with petroleum ether, the crystallization product is suction-filtered, and the 2-oxo-piperidine-1-(N-2-phenylethyl)-carboxamide so obtained is recrystallized from di-isopropyl ether: m.p. 66°-67° C. 49.2 g of 2-oxo-piperidine-1-(N-2-phenylethyl)-carboxamide are introduced in portions at 30° C. into 140 g of chlorosulfonic acid, and agitated for 1 hour at 40° C.

The clear, viscous solution is given dropwise onto ice, the sulfonic acid chloride is suction-filtered (m.p. 134°-136° C.), introduced into 750 ml of concentrated ammonia, and heated for 30 minutes on a steam bath. The 4-[2-(2-oxo-piperidine-1-carboxamido)-ethyl]-benzenesulfonamide is suction-filtered, and recrystallized from isopropanol: m.p. 173°-174° C.

3.3 g of sulfonamide, 80 ml of acetone and 2.8 g of K₂CO₃ are refluxed with agitation for 6 hours. Subsequently 1.3 g of cyclohexyl-isocyanate are added dropwise, and agitation is continued for 6 hours at boiling temperature. After standing overnight, the product is suction-filtered, the crystals obtained are treated with dilute hydrochloric acid, and again suction-filtered. The N-(4-[2-(2-oxo-piperidine-1-carboxamido)-ethyl]-benzenesulfonyl)-N'-cyclohexyl urea obtained with good yield is reprecipitated from highly dilute aqueous ammonia/dilute hydrochloric acid, and recrystallized from aqueous methanol; m.p. 197°-199° C.

In analogous manner, there are obtained:
N-(4-[2-(2-oxo-piperidine-1-carboxamido)-ethyl]benzenesulfonyl)-N'-4-methyl-cyclohexyl urea
m.p. 180°-182° C. (from aqu. ethanol).
N-(4-[2-(2-oxo-piperidine-1-carboxamido)-ethyl]benzenesulfonyl)-N'-butyl urea
m.p. 156°-158° C. (from acetone/water).
N-(4-[2-(2-oxo-piperidine-1-carboxamido)-ethyl]benzenesulfonyl)-N'-cyclopentyl urea
m.p. 167°-169° C. (from aqu. methanol).
N-(4-[2-(2-oxo-piperidine-1-carboxamido)-ethyl]benzenesulfonyl)-N'-isobutyl urea
m.p. 179°-181° C. (from acetone/water).

N-(4-[2-(2-oxo-piperidine-1-carboxamido)-ethyl]benzenesulfonyl)-N'-cyclooctyl urea
m.p. 170°–172° C. (from acetone/water).

EXAMPLE 3

N-(4-[2-(2-oxo-piperidine-1-carboxamido)-ethyl]benzenesulfonyl)-N'-3,4-dimethyl-cyclohexyl urea 2.3 g of N-(4-[2-(2-oxo-piperidine-1-carboxamido)ethyl]-benzene-sulfonyl)-carbamic acid methyl ester (m.p. 167°–169° C., prepared from the corresponding sulfonamide with chloroformic acid methyl ester and acetone in the presence of potassium carbonate), 50 ml of dioxan and 0.8 g of 3,4-dimethyl-cyclohexylamine are refluxed for 1 hour. The solvent is distilled off under reduced pressure, the residue reprecipitated from highly dilute ammonia/dilute hydrochloric acid, and the N-(4-[2-(2-oxo-piperidine-1-carboxamido)-ethyl]-benzenesulfonyl)-N'-3,4-dimethyl-cyclohexyl urea obtained with good yield is recrystallized from acetone/water; m.p. 139°–141° C.

In analogous manner, there are obtained:

N-(4-[2-(2-oxo-piperidine-1-carboxamido)-ethyl]benzenesulfonyl)-N'-methyl-cyclopentyl-methyl urea
m.p. 172°–174° C. (from acetone/water).

N-(4-[2-(2-oxo-piperidine-1-carboxamido)-ethyl]benzenesulfonyl)-N'-nortricyclyl urea
m.p. 179°–181° C. (from acetone/water).

N-(4-[2-(2-oxo-piperidine-1-carboxamido)-ethyl]benzenesulfonyl)-N'-bicyclo[2.2.1]hept-5-en-2-yl-methyl urea
m.p. 184°–186° C. (from acetone/water).

N-(4-[2-(2-oxo-piperidine-1-carboxamido)-ethyl]benzenesulfonyl)-N'-hexyl urea
m.p. 142°–144° C. (from acetone/water).

N-(4-[2-(2-oxo-piperidine-1-carboxamido)-ethyl]benzenesulfonyl)-N'-3-methyl-cyclopentyl urea
m.p. 166°–168° C. (from acetone/water).

N-(4-[2-(2-oxo-piperidine-1-carboxamido)-ethyl]benzenesulfonyl)-N'-cyclohex-3-enyl-methyl urea (x ½H₂O)
m.p. 136°–138° C. (from acetone/water).

N-(4-[2-(2-oxo-piperidine-1-carboxamido)-ethyl]benzenesulfonyl)-N'-4-isopropyl-cyclohexyl urea
m.p. 158°–160° C. (from acetone/water).

EXAMPLE 4

N-(4-[2-(2-oxo-hexamethylene-imine-1-carboxamido)-ethyl]-benzenesulfonyl)-N'-cyclohexyl urea 28.2 g of caprolactam and 37 g of 2-phenylmethyl isocyanate are heated for 2 hours at 150° C. in an oil bath, the reaction mixture is poured onto water, the 2-oxo-hexamethylene-imine-1-(N-2-phenylethyl)-carboxamide is suction-filtered, dried and recrystallized from petroleum ether; m.p. 65°–67° C. 43 g of this compound are introduced at about 30° C. in portions into 80 ml of chlorosulfonic acid. Agitation is continued for 1 hour at 50° C., the batch is cooled, and the reaction mixture is given dropwise into icewater. 300 ml of concentrated ammonia are added to the sulfonic acid chloride obtained as oily precipitate, and the mixture is heated for 30 minutes on a steam bath. The sulfonamide obtained is suction-filtered and dried; m.p. 176°–178° C. (from dilute methanol).

3.4 g of 4-[2-(2-oxo-hexamethylene-imine-1-carboxamido)-ethyl]-benzenesulfonamide, 150 ml of acetone and 2.8 g of K₂CO₃ are refluxed with agitation for 6 hours. Subsequently, 1.3 g of cyclohexyl-isocyanate are added dropwise, and agitation is continued for 6 hours at boiling temperature.

The potassium salt of the urea is suction-filtered, dissolved in water, the solution is filtered, and the filtrate is acidified with dilute hydrochloric acid. The sulfonyl urea obtained with good yield is suction-filtered, reprecipitated from highly dilute aqueous ammonia/dilute hydrochloric acid, and recrystallized from ethanol; m.p. 179°–181° C.

In analogous manner, there are obtained:

N-(4-[2-(2-oxo-hexamethylene-imine-1-carboxamido)-ethyl]-benzenesulfonyl)-N'-4-methyl-cyclohexyl urea
m.p. 181°–182° C. (from acetone/water).

N-(4-[2-(2-oxo-hexamethylene-imine-1-carboxamido)-ethyl]-benzenesulfonyl)-N'-butyl urea
m.p. 117°–119° C. (from ethanol).

N-(4-[2-(2-oxo-hexamethylene-imine-1-carboxamido)-ethyl]-benzenesulfonyl)-N'-4-ethyl-cyclohexyl urea
m.p. 162°–164° C. (from dil. acetone).

N-(4-[2-(2-oxo-hexamethylene-imine-1-carboxamido)-ethyl]-benzenesulfonyl)-N'-3-methyl-cyclopentyl urea
m.p. 161°–163° C. (from dil. acetone).

EXAMPLE 5

N-(4-[2-(2-oxo-hexamethylene-imine-1-carboxamido)-ethyl]-benzenesulfonyl)-N'-cyclopentyl urea 4 g of N-(4-[2-(2-oxo-hexamethylene-imine-1-carboxamido)-ethyl]-benzenesulfonyl)-carbamic acid methyl ester (m.p. 146°–148° C., prepared from the sulfonamide with chloroformic acid methyl ester and potassium carbonate in acetone at boiling temperature), 100 ml of dioxan and 0.9 g of cyclopentylamine are refluxed for 1 hour. The solvent is distilled off under reduced pressure, the residue is reprecipitated from highly dilute aqueous ammonia/dilute hydrochloric acid. The N-(4-[2-(2-oxo-hexamethylene-imine-1-carboxamido)-ethyl]-benzenesulfonyl)-N'-cyclopentyl urea obtained with good yield is suction-filtered and recrystallized from acetone/water; m.p. 148°–150° C.

In analogous manner, there are obtained:

N-(4-[2-(2-oxo-hexamethylene-imine-1-carboxamido)-ethyl]-benzenesulfonyl)-N'-4-hexyl urea
m.p. 142°–144° C. (from acetone/water).

N-(4-[2-(2-oxo-hexamethylene-imine-1-carboxamido)-ethyl]-benzenesulfonyl)-N'-4-isopropyl-cyclohexyl urea
m.p. 173°–175° C. (from dil. acetone).

EXAMPLE 6

N-(4-[2-(1-oxo-1,2,3,4,5,6,7,8-octahydro-isoquinoline-2-carboxamido)-ethyl]-benzenesulfonyl)-N'-cyclohexyl urea 1.9 g of 4-(2-[1-oxo-1,2,3,4,5,6,7,8-octahydro-isoquinoline-2-carboxamido]-ethyl)-benzenesulfonamide (m.p. 140°–142° C., prepared from 1-oxo-1,2,3,4,5,6,7,8-octahydro-isoquinoline-2-(N-2-phenylethyl)-carboxamide [m.p. 47° C., prepared by reaction of 1-oxo-1,2,3,4,5,6,7,8-octahydro-isoquinoline and phenylethyl isocyanate] with chlorosulfonic acid and reaction of the sulfochloride obtained with ammonia) are refluxed with agitation for 4 hours in 80 ml of acetone after addition of 1.4 g of ground potassium carbonate. After a short cooling, a solution of 0.7 g of cyclohexyl-isocyanate in a small amount of acetone is added dropwise, and agitation is continued for 4 hours with reflux. The suspension is evaporated, the residue dissolved in water, and the solution is acidified with 2 N hydrochloric acid. The precipitate is suction-filtered and, after reprecipitation from dilute ammonia solution, recrystallized with 2 N hydrochloric acid from ethanol. The N-(4-[2-(1-oxo-1,2,3,4,5,6,7,8-octahydro-isoquinoline-2-carboxamido)-ethyl]-benzenesulfonyl)-N'-cyclohexyl urea so obtained has a melting point of 176°–177° C.

In analogous manner, there is obtained:

N-(4-[2-(1-oxo-1,2,3,4,5,6,7,8-octahydro-isoquinoline-2-carboxamido)-ethyl]-benzenesulfonyl)-N'-4-methylcyclohexyl urea m.p. 180°–182° C. (from ethanol).

EXAMPLE 7

N-(4-[2-(1-oxo-hexahydro-iso-indoline-2-carboxamido)-ethyl]-benzenesulfonyl)-N'-cyclohexyl urea 2.74 g of 4-(2-[1-oxo-hexahydro-iso-indoline-2-carboxamido]-ethyl)-benzenesulfonamide (m.p. 145°–147° C., prepared from 1-oxo-hexahydro-iso-indolin-2-yl-(N-2-phenylethyl)-carboxamide [m.p. 65°–68° C., obtained by reaction of 1-oxo-hexahydro-iso-indoline and phenylethyl-isocyanate] with chlorosulfonic acid and reaction of the sulfochloride so obtained with ammonia) are refluxed with agitation for 3 hours in 50 ml of acetone and 25 ml of dioxan after addition of 2.1 g of potassium carbonate. After a short cooling, a solution of 1.1 g of cyclohexyl-isocyanate in a small amount of acetone is added dropwise, and refluxing is continued for another 4 hours. The cold suspension is concentrated in vacuo, the residue is dissolved in water, and the solution is acidified with 2 N hydrochloric acid. After suction-filtration from dilute ammonia solution, the precipitate is reprecipitated with 2 N hydrochloric acid, and recrystallized from ethanol. The N-(4-[2-(1-oxo-hexahydro-iso-indoline-2-carboxamido)-ethyl]-benzenesulfonyl)-N'-cyclohexyl urea so obtained has a melting point of 139°–140° C.

In analogous manner, there is obtained:

N-(4-[2-(1-oxo-hexahydro-iso-indoline-2-carboxamido)-ethyl]-benzenesulfonyl)-N'-(4-methyl-cyclohexyl)urea m.p. 153°–155° C. (from ethanol).

EXAMPLE 8

N-(4-[2-(4-methyl-2-oxo-piperidine-1-carboxamido)-ethyl]-benzenesulfonyl)-N'-cyclohexyl urea According to Example 2, the 4-methyl-2-oxo-piperidine-1-(N-2-phenylethyl)-carboxamide having a melting point of 63° C. is obtained from 4-methyl-2-oxo-piperidine and 2-phenylethyl isocyanate, subsequently the 4-[2-(4-methyl-2-oxo-piperidine-1-carboxamido)-ethyl]-benzenesulfochloride, m.p. 99°–101° C. from the above compound by reaction with chlorosulfonic acid, and then the corresponding sulfonamide by reaction with ammonia (m.p. 149°–151° C.), and furthermore N-(4-[4-methyl-2-oxo-piperidine-1-carboxamido)-ethyl]-benzenesulfonyl)-N'-cyclohexyl urea m.p. 177°–178° C. (from dil. acetone) with the use of cyclohexylisocyanate.

In analogous manner, there are obtained from the sulfonamide:

N-(4-[2-(4-methyl-2-oxo-piperidine-1-carboxamido)-ethyl]-benzenesulfonyl)-N'-4-methylcyclohexyl urea m.p. 190°–191° C. (from dil. acetone).

N-(4-[2-(4-methyl-2-oxo-piperidine-1-carboxamido)-ethyl]-benzenesulfonyl)-N'-butyl urea m.p. 159°–161° C. (from dil. acetone).

N-(4-[2-(4-methyl-2-oxo-piperidine-1-carboxamido)-ethyl]-benzenesulfonyl)-N'-4-ethylcyclohexyl urea m.p. 178°–180° C. (from dil. methanol).

N-(4-[2-(4-methyl-2-oxo-piperidine-1-carboxamido)-ethyl]-benzenesulfonyl)-N'-4-methylcyclohex-3-enyl urea m.p. 173°–175° C. (from dil. acetone).

EXAMPLE 9

N-(4-[2-(4-methyl-2-oxo-piperidine-1-carboxamido)-ethyl]-benzenesulfonyl)-N'-4-cyclopentyl urea According to Example 3, N-(4-[2-(4-methyl-2-oxo-piperidine-1-carboxamido)-ethyl]-benzenesulfonyl)-N'-4-cyclopentyl urea, m.p. 177°–179° C. (from dil. methanol) is obtained from N-(4-[2-4-methyl-2-oxo-piperidine-1-carboxamido)-ethyl]-benzenesulfonyl)-carbamic acid methyl ester (m.p. 137°–139° C., prepared from the 4-[2-(4-methyl-2-oxo-piperidine-1-carboxamido)-ethyl]-benzenesulfonamide cited in Example 8 by reaction with chloroformic acid ester.

In analogous manner, there are obtained:

N-(4-[2-(4-methyl-2-oxo-piperidine-1-carboxamido)-ethyl]-benzenesulfonyl)-N'-4-isopropylcyclohexyl urea m.p. 171°–173° C. (from methanol).

N-(4-[2-(4-methyl-2-oxo-piperidine-1-carboxamido)-ethyl]-benzenesulfonyl)-N'-cycloheptyl urea m.p. 142°–143° C. (from dil. ethanol).

N-(4-[2-(4-methyl-2-oxo-piperidine-1-carboxamido)-ethyl]-benzenesulfonyl)-N'-3-methyl-cyclopentyl urea m.p. 145°–147° C. (from dil. acetone).

N-(4-[2-(4-methyl-2-oxo-piperidine-1-carboxamido)-ethyl]-benzenesulfonyl)-N'-bicyclo[2.2.1]-hept-5-en-2-yl-methyl urea m.p. 164°–166° C. (from dil. acetone).

N-(4-[2-(4-methyl-2-oxo-piperidine-1-carboxamido)-ethyl]-benzenesulfonyl)-N'-3-methylcyclopentylmethyl urea m.p. 152°–154° C. (from dil. acetone).

N-(4-[2-(4-methyl-2-oxo-piperidine-1-carboxamido)-ethyl]-benzenesulfonyl)-N'-adamantyl urea m.p. 176°–178° C. (from dil. acetone).

EXAMPLE 10

N-(4-[2-(3-butyl-4-methyl-2-oxo-piperidine-1-carboxamido)-ethyl]-benzenesulfonyl)-N'-cyclohexyl urea 3-butyl-4-methyl-2-oxo-piperidine (m.p. 95°–98° C., prepared according to German Offenlegungsschrift No. 1,023,464) is converted according to Example 2 with phenylethyl-isocyanate to 3-butyl-4-methyl-2-oxo-piperidine-1-(N-2-phenylethyl)-carboxamide, this crude product is converted with chlorosulfonic acid to the sulfochloride, the sulfochloride is converted with ammonia to 4-(2-[3-butyl-4-methyl-2-oxo-piperidine-1-carboxamido)-ethyl]-benzenesulfonamide, m.p. 165°–167° C., from which there is obtained with cyclohexyl isocyanate with N-(4-[2-(3-butyl-4-methyl-2-oxo-piperidine-1-carboxamido)-ethyl]-benzenesulfonyl)-N'-cyclohexyl urea, m.p. 123°–125° C. (from methanol).

In analogous manner, the following compound is obtained from the sulfonamide:

N-(4-[2-(3-butyl-4-methyl-2-oxo-piperidine-1-carboxamido)-ethyl]-benzenesulfonyl)-N'-4-methylcyclohexyl urea.

m.p. 131°–133° C. (from methanol).

EXAMPLE 11

N-(4-[2-(3,4-dimethyl-2-oxo-3-pyrroline-1-carboxamido)-ethyl]-benzenesulfonyl)-N'-cyclohexyl urea According to Example 2, there is prepared from 3,4-dimethyl-2-pyrrolone and 2-phenylethyl-isocyanate and 3,4-dimethyl-2-oxo-pyrroline-1-(N-2-phenylethyl)-carboxamide; m.p. 132°-134° C., then with chlorosulfonic acid the sulfochloride, m.p. 189°-190° C., subsequently from the sulfochloride with ammonia the sulfonamide, m.p. 232°-234° C., and the cyclohexyl isocyanate from the sulfonamide the
N-(4-[2-(3,4-dimethyl-2-oxo-3-pyrroline-1-carboxamido)-ethyl]-benzenesulfonyl)-N'-cyclohexyl urea
m.p. 200°-202° C. (from methanol/dioxan).

In analogous manner, there are obtained from the sulfonamide:
N-(4-[2-(3,4-dimethyl-2-oxo-3-pyrroline-1-carboxamido)-ethyl]-benzenesulfonyl)-N'-4-methyl-cyclohexyl urea
m.p. 208°-210° C. (from dil. methanol).
N-(4-[2-(3,4-dimethyl-2-oxo-3-pyrroline-1-carboxamido)-ethyl]-benzenesulfonyl)-N'-butyl urea
m.p. 198°-200° C. (from methanol/dioxan).

EXAMPLE 12

N-(4-[2-(4-methyl-2-oxo-3-pyrroline-1-carboxamido)-ethyl]-benzenesulfonyl)-N'-cyclohexyl urea According to Example 2, from 4-methyl-2-pyrrolone and 2-phenylethyl-isocyanate, there is obtained the 4-methyl-2-oxo-3-pyrroline-1-(N-2-phenylethyl).carboxamide, m.p. 94°-96° C., therefrom the sulfochloride, m.p. 193°-195° C., with the use of chlorosulfonic acid, from the sulfochloride the sulfonamide, m.p. 196°-198° C., and from the sulfonamide the N-(4-[2-(4-methyl-2-oxo-3-pyrroline-1-carboxamido)-ethyl]-benzenesulfonyl)-N'-cyclohexyl urea
m.p. 195°-197° C. (from dil. methanol/dioxan) is obtained with cyclohexyl isocyanate.

In analogous manner, there are obtained from the sulfonamide:
N-(4-[2-(4-methyl-2-oxo-3-pyrroline-1-carboxamido)-ethyl]-benzenesulfonyl)-N'-4-methyl-cyclohexyl urea
m.p. 199°-201° C. (from dil. dioxan).
N-(4-[2-(4-methyl-2-oxo-3-pyrroline-1-carboxamido)-ethyl]-benzenesulfonyl)-N'-butyl urea
m.p. 189°-191° C. (from dil. methanol/dioxan).

EXAMPLE 13

N-(4-[2-(2-oxo-piperidine-1-carboxamido)-propyl]-benzenesulfonyl)-N'-cyclohexyl urea 1.6 g of 4-[2-(2-oxo-piperidine-1-carboxamido)-propyl]-benzenesulfonamide (m.p. 165°-167° C., prepared from 4-(2-aminopropyl)-benzenesulfonamide and 2-oxo-piperidine-1-carboxylic acid chloride, which for its part is obtained from the Na compound of 2-oxo-piperidine and phosgene) are refluxed with agitation for several hours in 100 ml of acetone with 2 g of ground potassium carbonate. Subsequently, 0.6 g of cyclohexyl-isocyanate is added, and refluxing is continued for a further 6 hours. The acetone is then evaporated under reduced pressure, the residue is treated with water and hydrochloric acid, the product is suction-filtered and reprecipitated from dilute ammonia. The N-(4-[2-(2-oxo-piperidine-1-carboxamido)-propyl]-benzenesulfonyl)-N'-cyclohexyl urea is recrystallized from dilute ethanol; m.p. 176°-177° C.

EXAMPLE 14

N-(4-[2-(4-methyl-2-oxo-piperidine-1-carboxamido)-ethyl]-benzenesulfonyl)-N'-cyclohexyl urea 1.2 g N-(4-[2-(4-methyl-2-oxo-piperidine-1-carboxamido)-ethyl]-benzenesulfonyl)-N'-cyclohexyl-thiourea (m.p. 179°-181° C., prepared from 4-[2-(4-methyl-2-oxo-piperidine-1-carboxamido)-ethyl]-benzenesulfonamide and cyclohexyl-isocyanate in acetone in the presence of potassium carbonate) are dissolved in 75 ml of acetone and 10 ml of water. At 0° C., a solution of 0.1 g of sodium nitrite in 5 ml of water is added to this solution, subsequently 0.8 ml of 5 N acetic acid is added dropwise, and agitation is continued for 2 hours at 0° C. Subsequently, the acetone is evaporated under reduced pressure, the product is suction-filtered and reprecipitated from dilute ammonia. After recrystallization from dilute acetone, N-(4-[2-(4-methyl-2-oxo-piperidine-1-carboxamido)-ethyl]-benzenesulfonyl)-N'-cyclohexyl urea has a melting point of 176°-178° C., and with the product prepared according to Example 8, shows no depression.

EXAMPLE 15

N-(4-[2-(4-methyl-2-oxo-piperidine-1-carboxamido)-ethyl]-benzenesulfonyl)-N'-cyclohexyl urea 0.5 g N-(4-[2-(4-methyl-2-oxo-piperidine-1-carboxamide)-ethyl]-benzenesulfonyl)-N'-cyclohexyl-isourea methyl ether (m.p. 138°-140° C., prepared by desulfurization of N-(4-[2-(4-methyl-2-oxo-piperidine-1-carboxamido)-ethyl]-benzenesulfonyl)-N'-cyclohexyl-thiourea with mercury oxide in the presence of methanol) is dissolved in 5 ml of dioxan, and heated for a short time on a steam bath with 2 ml of concentrated hydrochloric acid. Subsequently, the water is added to the reaction mixture, the product is suction-filtered, reprecipitated from dilute ammonia and recrystallized from dilute acetone. The N-(4-[2-(4-methyl-2-oxo-piperidine-1-carboxamido)-ethyl]-benzenesulfonyl)-N'-cyclohexyl urea obtained has a melting point of 176°-178° C. and, with the substance obtained according to Example 8, shows no depression.

EXAMPLE 16

N-(4-[2-(4-methyl-2-oxo-piperidine-1-carboxamido)-ethyl]-benzenesulfonyl)-N'-cyclohexyl urea 0.5 g N-(4-[2-(4-methyl-2-oxo-piperidine-1-carboxamido)-ethyl]-benzenesulfonyl)-N'-cyclohexyl-isothiourea methyl ether (m.p. 167°-169° C., prepared by methylation of N-(4-[2-(4-methyl-2-oxo-piperidine-1-carboxamido)-ethyl]-benzenesulfonyl)-N'-cyclohexyl thiourea with methyl iodide) in 30 ml of tetrahydrofuran is combined with 2 ml of 2 N NaOH and heated for a few minutes on a steam bath. Subsequently, the batch is diluted with water, the tetraydrofuran is distilled off under reduced pressure, and the batch is acidified with dilute hydrochloric acid. The product is suction-filtered, reprecipitated from dilute ammonia and recrystallized from dilute acetone. The N-(4-[2-(4-methyl-2-oxo-piperidine-1-carboxamido)-ethyl]-benzenesulfonyl)-N'-cyclohexyl urea obtained has a melting point of 175°-177° C., and, with the substance obtained according to Example 8, shows no depression.

EXAMPLE 17

N-(4-[2-(4-methyl-2-oxo-piperidine-1-carboxamido)-ethyl]-benzenesulfonyl)-N'-cyclohexyl urea 1.6 g of N-(4-[2-amino-ethyl]-benzenesulfonyl)-N'-cyclohexyl urea and 0.2 g of sodium hydroxide are dissolved in 10 ml of water and 50 ml of acetone. With agitation and ice cooling, a solution of 0.85 g of 4-methyl-2-oxo-piperidine-1-carboxylic acid chloride (prepared by reaction of the sodium compound of 4-methyl-2-oxo-piperidine with phosgene) in 20 ml of acetone is added dropwise to this solution, and agitation is continued for 2 hours at room temperature. Subsequently, the acetone is evaporated under reduced pressure, the batch is acidified, suction-filtered, the product is reprecipitated from dilute ammonia and recrystallized from dilute acetone. The N-(4-[2-(4-methyl-2-oxo-piperidine-1-carboxamido)-ethyl]-benzenesulfonyl)-N'-cyclohexyl urea obtained has a melting point of 177°–178° C. and is identical with the product obtained according to Example 8.

EXAMPLE 18

N-(4-[2-(4-methyl-2-oxo-piperidine-1-carboxamido)-ethyl]-benzenesulfonyl)-N'-butyl urea 0.6 g of 4-[2-(4-methyl-2-oxo-piperidine-1-carboxamido)-ethyl]-benzenesulfinic acid (crude product m.p. 113°–115° C., prepared by reaction of 4-[2-(4-methyl-2-oxo-piperidine-1-carboxamido)-ethyl]-benzenesulfochloride with sodium sulfite) and 0.3 g of N-hydroxy-N'-butyl urea are dissolved in 50 ml of dioxan. 0.4 g of thionyl chloride in 10 ml of dioxan is added dropwise to this solution, and the batch is heated for 2 hours at 60° C. Subsequently, the solvent is evaporated under reduced pressure, water is added dropwise to the residue, the oily substance is separated and reprecipitated from ammonia. The N-(4-[2-(4-methyl-2-oxo-piperidine-1-carboxamido)-ethyl]-benzenesulfonyl)-N'-butyl urea obtained has a melting point of 155°–157° C., and, with the substance obtained according to Example 8, shows no depression.

EXAMPLE 19

N-(4-[2-(3-ethyl-4-methyl-2-oxo-3-pyrroline-1-carboxamido)-ethyl]-benzenesulfonyl)-N'-cyclohexyl urea According to Example 2, from 3-ethyl-4-methyl-2-pyrrolone and 2-phenylethyl-isocyanate there is obtained 3-ethyl-4-methyl-2-oxo-3-pyrroline-1-(N-2-phenylethyl)-carboxamide, m.p. 106°–108° C., therefrom the sulfochloride, m.p. 172°–175° C., with chlorosulfonic acid, from the sulfochloride the sulfonamide, m.p. 180°–182° C., with ammonia, and from the sulfonamide, using cyclohexyl isocyanate, the N-(4-[2-(3-ethyl-4-methyl-2-oxo-3-pyrroline-1-carboxamido)-ethyl]-benzenesulfonyl)-N'-cyclohexyl urea, m.p. 185°–187° C. (from dil. acetone).

In analogous manner, there are obtained from the sulfonamide:
N-(4-[2-(3-ethyl-4-methyl-2-oxo-3-pyrroline-1-carboxamido)-ethyl]-benzenesulfonyl)-N'-4-methyl-cyclohexyl urea,
m.p. 168°–170° C. (from dil. acetone).
N-(4-[2-(3-ethyl-4-methyl-2-oxo-3-pyrroline-1-carboxamido)-ethyl]-benzenesulfonyl)-N'-butyl urea, m.p. 151°–153° C. (from methanol).

EXAMPLE 20

N-(4-[2-(3-butyl-4-methyl-2-oxo-3-pyrroline-1-carboxamido)-ethyl]-benzenesulfonyl)-N'-cyclohexyl urea According to Example 2, there is obtained from 3-butyl-4-methyl-2-pyrrolone (m.p. 95°–97° C., prepared acc. to A. 598, 198 (1956)) and 2-phenylethyl-isocyanate the 3-butyl-4-methyl-2-oxo-3-pyrroline-1-(N-2-phenylethyl)-carboxamide, m.p. 90°–91° C., therefrom the sulfochloride using chlorosulfonic acid, from the crude sulfochloride the sulfonamide, m.p. 132°–134° C., with the use of ammonia, and from the sulfonamide, using cyclohexyl-isocyanate, the N-(4-[2-(3-butyl-4-methyl-2-oxo-3-pyrroline-1-carboxamido)-ethyl]-benzenesulfonyl)-N'-cyclohexyl urea, m.p. 173°–175° C. (from dil. methanol).

In analogous manner, there are obtained from the sulfonamide:
N-(4-[2-(3-butyl-4-methyl-2-oxo-3-pyrroline-1-carboxamido)-ethyl]-benzenesulfonyl)-N'-4-methyl-cyclohexyl urea
m.p. 178°–180° C. (from dil. methanol).
N-(4-[2-(3-butyl-4-methyl-2-oxo-3-pyrroline-1-carboxamido)-ethyl]-benzenesulfonyl)-N'-butyl urea, m.p. 127°–129° C. (from dil. methanol).

In analogous manner, there is obtained from the sulfonamide mentioned in example 11 the
N-(4-[2-(3,4-dimethyl-2-oxo-3-pyrroline-1-carboxamido)-ethyl]-benzenesulfonyl)-N'-4-ethyl-cyclohexyl urea
m.p. 203°–205° C. (from methanol/dioxan).

What is claimed is:
1. A sulfonyl urea of the formula

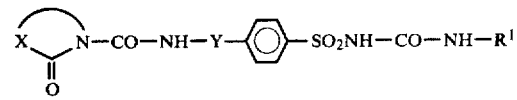

or a physiologically acceptable salt thereof, wherein
X is alkylene or alkenylene having from 3 to 6 carbon atoms, optionally substituted by up to 3 alkyl groups each having from 1 to 4 carbon atoms, or by phenyl;
or the group

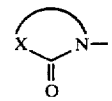

is a bicyclic system of the formula

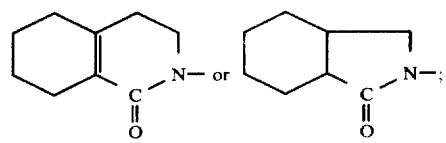

and
Y is alkylene having 2 or 3 carbon atoms;
R[1] is alkyl having from 4 to 6 carbon atoms, cycloalkyl, alkylcycloalkyl, dialkylcycloalkyl, cycloalkylalkyl, cycloalkenyl, or alkylcycloalkenyl in each case having 4 to 9 carbon atoms, or is methylcyclopentylmethyl, cyclohexenylmethyl, chlorocyclohexyl, methoxycyclohexyl, bicycloheptyl, bicycloheptenyl, bicycloheptylmethyl, bicycloheptenylmethyl, bicyclooctyl, nortricyclyl, adamantyl, or benzyl.

2. A compound as in claim 1 which is N-(4-[2-(3,4-dimethyl-2-oxo-3-pyrroline-1-carboxamido)-ethyl]-benzenesulfonyl)-N'-4-methyl-cyclohexyl-urea.

3. A compound as in claim 1 which is N-(4-[2-(3-ethyl-4-methyl-2-oxo-3-pyrroline-1-carboxamido)-ethyl]-benzenesulfonyl)-N'-4-methyl-cyclohexyl-urea.

4. A compound as in claim 1 which is N-(4-[2-(3,4-dimethyl-2-oxo-3-pyrroline-1-carboxamido)-ethyl]-benzenesulfonyl)-N'-4-ethyl-cyclohexyl-urea.

5. A pharmaceutical composition for lowering the blood sugar level, which comprises a hypoglycemically effective amount of a sulfonyl urea or salt thereof as in claim 1 in combination with a pharmaceutically acceptable carrier therefor.

6. A method for lowering the blood sugar level in a patient suffering from diabetes, which comprises orally administering a hypoglycemically effective amount of a sulfonyl urea or salt thereof as claimed in claim 1.

* * * * *